_[19]_ United States Patent _[11]_ Patent Number: 5,457,033
Engels et al. _[45]_ Date of Patent: Oct. 10, 1995

[54] PREPARATION OF POLYPEPTIDES HAVING AN AMIDE CARBOXYL TERMINAL END

[75] Inventors: Joachim Engels, Kronberg/Taunus; Wolfgang König, Hofheim am Taunus; Hubert Müllner, Kelkheim; Eugen Uhlmann, Königstein/Taunus; Waldemar Wetekam, Eppstein/Taunus, all of Germany

[73] Assignee: Hoechst Aktiengesellschaft, Frankfurt am Main, Germany

[21] Appl. No.: 205,816

[22] Filed: Mar. 4, 1994

Related U.S. Application Data

[63] Continuation of Ser. No. 336,510, Apr. 12, 1989, abandoned, which is a continuation of Ser. No. 634,271, Jul. 25, 1984, abandoned.

[30] Foreign Application Priority Data

Jul. 27, 1983 [DE] Germany ........................ 33 27 007.4

[51] Int. Cl.$^6$ .......................... C12N 15/16; C12N 15/62; C12N 15/70; C12P 21/06
[52] U.S. Cl. ..................... 435/69.1; 435/68.1; 435/69.4; 435/69.8; 435/71.2; 435/172.3; 435/252.3; 435/252.33; 435/320.1; 536/23.4; 536/23.51
[58] Field of Search .................... 435/68.1, 69.1, 435/69.4, 69.8, 71.2, 172.3, 252.3, 252.33, 320.1; 536/23.51, 23.4

[56] References Cited

FOREIGN PATENT DOCUMENTS 0191869  2/1986  European Pat. Off. .

OTHER PUBLICATIONS

Guillemin et al., Science, 218: 585–587 (1982).
Bradbury et al., Nature, 298: 686–688 (1982).
Husain et al., FEBS Letters, 152: 277–281 (1983).
Gait et al., Nucleic Acids Res., 8: 1081–1096 (1980).
Amann et al., Gene, 25: 167–178 (1983).
Gubler et al. 1983. Proc. Natl. Acad. Sci. USA 80:4311–4314.
Bradbury et al. 1982. Nature 298: 686–688.
Smith et al. 1982. Nucleic Acids Research 10(150) 4467–4482.

*Primary Examiner*—David T. Fox
*Attorney, Agent, or Firm*—Finnegan, Henderson, Farabow, Garrett & Dunner

[57] ABSTRACT

Polypeptides having a carboxamide carboxyl terminal end and a methionine residue, which is optionally bonded to a bacterial protein, on the amino end can be prepared by synthesis by genetic engineering methods of the corresponding polypeptide having at the C terminal end a glycine residue, and conversion of the latter enzymatically into the amino group of the desired carboxamide group. Peptides which have the aminoacid sequence of growth hormone releasing factor, part sequences thereof, or modifications of these peptides, are readily accessible by this means. The synthesis by genetic engineering methods is advantageously carried out via two gene fragments which are synthesized chemically from smaller, single-stranded structural units. The two gene fragments are then linked enzymatically to give the complete gene, which is incorporated into a suitable vector, amplified there, and the peptide is isolated directly or as a fused protein, and is converted enzymatically into the desired amide.

30 Claims, 1 Drawing Sheet

PREPARATION OF POLYPEPTIDES HAVING AN AMIDE CARBOXYL TERMINAL END

This application is a continuation, of application Ser. No. 07/336,510, filed Apr. 12, 1989, now abandoned, which is a continuation of application Ser. No. 06/634,271, filed Jul. 25, 1984, now abandoned.

BACKGROUND AND SUMMARY OF THE INVENTION

The invention relates to a process for the preparation of polypeptides having a carboxamide carboxyl terminal end, to new peptides of this class, and to gene structures, plasmids and host organisms suitable for this purpose.

The direct synthesis of polypeptides having a carboxamide carboxyl terminal end by genetic engineering methods is not possible. However, a large number of natural peptides having a carboxamide terminal end have been isolated, such as PHI, VIP, CRF, nerve growth factor, oxytocin, cholecystokinin, gastrin, calcitonin, vasopressin, mellitin, melanotropin and, in particular, the growth hormone releasing factor, called "GRF" in the following text. The invention particularly relates to the preparation of peptides having the aminoacid sequence of GRF and of modified peptides similar to GRF, and of part sequences of these peptides. For this reason, in the following text, first the nature of the invention is illustrated by the preparation of peptides having the aminoacid sequence of GRF and of modified GRF derivatives:

DETAILED DESCRIPTION OF THE INVENTION

Figure 1:
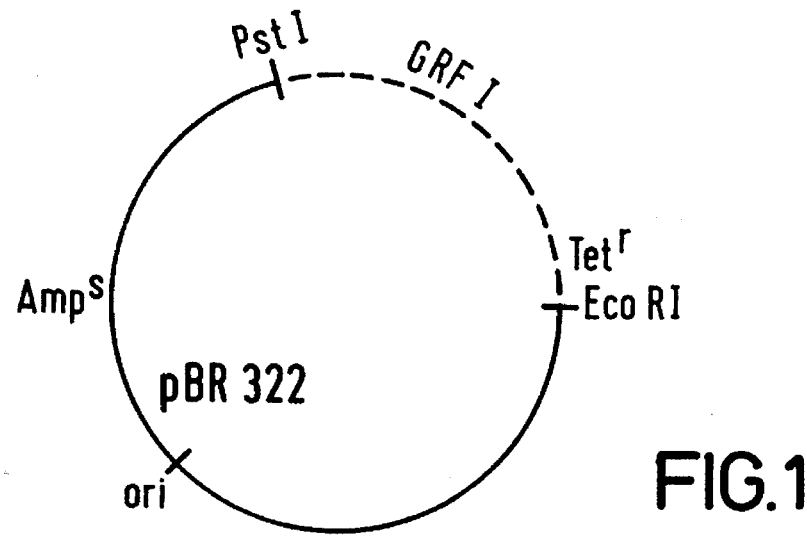
FIG. 1 shows the incorporation of gene fragment I of the GRF gene into plasmid pBR 322.

GRF is formed in the hypothalamus and stimulates the secretion of growth hormone in the pituitary. However, hitherto it has not been possible to isolate and characterize GRF from extracts of human hypothalamus. It has been possible, however, to isolate from a human pancreatic tumor a peptide having 44 aminoacids which shows GRF activity in vitro and in vivo (R. Guillemin et al., Science 218 (1982) 585–587). This peptide has the following aminoacid sequence:

H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser- Arg-Gln-Gln-Gly-Glu-Ser-Asn-Gln-Glu-Arg-Gly-Ala-Arg-Ala-Arg-Leu-NH$_2$.

As is well known, the genetic code is "degenerate", i.e. only two aminoacids are coded for by a single nucleotide sequence, while 2 to 6 triplets are assigned to the remaining 18 genetically codable aminoacids. Thus, there is an immense variety of possibilities for the codons for the synthesis of the gene. It has now been found that the DNA sequence I is particularly advantageous.

An "overlapping" DNA sequence is located at the 5' end of the coding strand, this corresponding to the restriction endonuclease EcoRI, while the single-stranded overlapping sequence at the 3' end of the coding strand corresponds to the restriction enzyme SalI. These two different recognition sequences guarantee the insertion of the DNA in plasmids in the desired orientation.

The codon for the aminoacid methionine (which is numbered 0 in the DNA sequence I) is located at the 5' end of the coding strand between these recognition sequences and the codons for the aminoacid sequence. At the end of this strand, the triplet coding for leucine is followed by the codon 45 for glycine and 2 termination triplets.

An internal unique cleavage site for the restriction enzyme PstI (in codon 24 of the coding strand or codon 23 of the non-coding strand) permits the subcloning of two gene fragments which can be incorporated into cloning vectors which have been well studied, such as pBR 322 or pUC 8. In addition, a number of other unique recognition sequences for restriction endonucleases have been incorporated within the structural gene, these, on the one hand, providing access to part sequences of GRF and, on the other hand, permitting mutations to be brought about:

| Restriction enzyme | Cut after nucleotide No. (coding strand) | Peptide fragment Aminoacid from to |
|---|---|---|
| Pvu II | 56 | 1–16 |
| Pst I | 79 | 1–24 |
| Xba I | 90 | 1–29 |
| Hinf I | 105 | 1–34 |
| Bst N I | 114 | 1–36 |
| Xho I | 127 | 1–41 |

The DNA sequence I can be constructed from 13 oligonucleotides ranging in length from 18 to 29 nucleotides by first synthesizing the latter chemically and then linking them together enzymatically via "sticky ends" of 4 to 6 nucleotides.

Furthermore, account was taken in DNA sequence of the fact that for those aminoacids to which several codons are assigned, the latter are not equivalent but, on the contrary, show different preferences in the particular host cell, such as E. coli. In addition, palindromic sequences were reduced to a minimum.

Thus, the DNA sequence I gene structure is readily accessible from relatively small structural units, permits the subcloning of two gene fragments into well-known vectors, and allows their expression in high yield. Depending on the incorporation of the synthetic gene in the cloning vector, the desired peptide having the amino-acid sequence of GRF is expressed directly or in the form of a protein fused with a bacterial protein, such as β-galactosidase. Fused proteins of this type are then cleaved chemically or enzymatically in a manner known per se.

An example of a part sequence which leads to a peptide having the first 16 aminoacids of GRF and a terminal carboxamide group (and a methionine residue at the amino end), is represented by a modified DNA sequence I in which the triplets Nos. 45–47 follow directly on triplet No. 16. Corresponding statements apply to the peptide fragments which are listed in the table above and have the aminoacids up to Nos. 24, 29, 34, 36 and 41. Moreover, a part sequence having the first 26 aminoacids, for example, can be prepared analogously.

An example which may be mentioned of a modified GRF is a polypeptide in which the methionine in position 27 is replaced by leucine, For this purpose, the triplet No. 27 in DNA sequence I is replaced by the following:

| 27 |
|---|
| Leu |
| CTG |
| GAC |

Further variations emerge from DNA sequence II, of which, for simplicity, only the coding strand is shown.

Thus, according to the invention, it is possible to prepare a polypeptide of the formula I $$Y-R-NH_2 \qquad (I)$$

in which Y denotes the methionine residue or the residue of a bacterial protein bonded via methionine, and R denotes a peptide sequence of genetically codable amino-acids, by producing, by genetic engineering methods, a polypeptide of the formula II $$Y-R-NH-CH_2-COOH \qquad (II)$$

and converting the product enzymatically into the polypeptide of the formula I.

When R denotes the aminoacid sequence of GRF, with Leu in position 27, the methionine at the amino end can be removed by cleavage with cyanogen bromide. If a fused protein is obtained in the synthesis by genetic engineering methods, then the undesired portion of the bacterial protein is also removed in the cleavage with cyanogen bromide.

The enzymatic conversion of the glycyl radical into the amino group of the carboxamide group is known per se (A. F. Bradbury et al., Nature 298 (1982) 686–688; I. Husain et al., FEBS Letters 152 (1983) 277–281).

The incorporation of the synthetic gene or gene fragments into cloning vectors, for example the plasmids pUC 8, pBR 322, pKK 177.3, ptac 11 and other commercial or generally accessible plasmids, is carried out in a manner known per se. In this context, reference may be made to the textbook by Maniatis (Molecular Cloning, Maniatis et al., Cold Spring Harbor, 1982).

The transfer of the hybrid plasmids thus obtained into suitable host organisms, preferably *E. coli*, is likewise known per se and described in detail in the textbook mentioned above. The isolation of the expressed protein, the cleavage with cyanogen bromide, and the working up are described by Guillemin (loc.cit.).

The polypeptides obtained according to the invention, which have the methionine residue at the amino end and/or the glycine residue at the carboxyl end, are new and the invention likewise relates to them. The same applies to the modified GRF derivatives according to DNA sequence II, to the DNA sequences. I and II, to the gene fragments mentioned, to the hybrid plasmids obtained with them, to the transformed host organisms, and to the expressed fused proteins.

Further embodiments of the invention are set out in the patent claims.

In the examples which follow, some embodiments of the invention are illustrated in detail, from which the variety of possible modifications and combinations will be evident to those skilled in the art. In these examples, the percentages relate to weight unless otherwise specified.

EXAMPLES

1. Chemical synthesis of a single-stranded oligonucleotide

The synthesis of the structural units of the gene is illustrated by example of structural unit Ia of the gene which comprises nucleotides 1–27 of the coding strand. The nucleoside located at the 3' end, in the present case adenosine (nucleotide No. 27), is covalently bonded via the 3'-hydroxyl group to silica gel (FRACTOSIL®, supplied by Merck) by known methods (M. J. Gait et al., Nucleic Acids Res. 8 (1980) 1081–1096). For this purpose, first the silica gel is reacted with 3-(triethoxysilyl)propylamine, with elimination of ethanol, producing an Si—O—Si bond. The adenosine, in the form of the $N^6$-benzoyl-3'-0-succinoyl-5'-dimethoxytrityl ether, is reacted with the modified support in the presence of paranitrophenol and N,N'-dicyclohexylcarbodiimide, the free carboxyl group of the succinoyl group acylating the amino radical of the propylamine group.

In the subsequent synthetic steps, the base component is used as the 5'-0-dimethoxytritylnucleoside 3'-phosphorous acid monomethyl ester dialkylamide or chloride, the adenine being in the form of the $N^6$-benzoyl compound, the cytosine in the form of the $N^4$-benzoyl compound, the guanine in the form of the $N^2$-isobutyryl compound, and the thymine, which contains no amino group, being without a protective group.

100 mg of the polymeric support, which contains 4 μmol of bound adenine, are treated consecutively with the following agents:

a) nitromethane b) saturated zinc bromide solution in nitromethane containing 1% water c) methanol d) tetrahydrofuran e) acetonitrile f) 80 μmol of the appropriate nucleoside phosphite and 400 μmol of tetrazole in 1 ml of anhydrous acetonitrile (5 minutes)

g) 20% acetic anhydride in tetrahydrofuran containing 40% lutidine and 10% dimethylaminopyridine (2 minutes)

h) tetrahydrofuran i) tetrahydrofuran containing 20% water and 40% lutidine j) 3% iodine in collidine/water/tetrahydrofuran in the ratio 5:4:1 by volume k) tetrahydrofuran and l) methanol.

In this context, "phosphite" is to be understood to be the deoxyribose 3'-monophosphorous acid monomethyl ester, the third valency being saturated by chlorine or a tertiary amino group, for example a morpholino radical. The yields in the individual steps of the synthesis can be determined in each case after the detritylation reaction (b) by spectrophotometry, measuring the absorption of the dimethoxytrityl cation at a wavelength of 496 nm.

After synthesis of the oligonucleotide is complete, the methyl phosphate protective groups in the oligomer are eliminated using p-thiocresol and triethylamine. Then the oligonucleotide is removed from the solid support by treatment with ammonia for 3 hours. Treatment of the oligomers with concentrated ammonia for 2 to 3 days quantitatively eliminates the amino protective groups on the bases. The crude product thus obtained is purified by high pressure liquid chromatography (HPLC) or by polyacrylamide gel electrophoresis.

The other structural units Ib–IIg of the gene are synthesized in an entirely corresponding manner, the sequence of nucleotides in which being clear from DNA sequence III.

2. Enzymatic linkage of the single-stranded oligonucleotides to give the gene fragments I and II For the phosphorylation of the oligonucleotides at the 5' terminal end, 1 nmol of each of oligonucleotides Ia and Ib are treated with 5 nmol of adenosine triphosphate and four units of T4-polynucleotide kinase in 20 µl of 50 mM tris.HCl buffer (pH 7.6), 10 mM magnesium chloride and 10 ml dithiothreitol (DTT) at 37° C. for 30 minutes.

The enzyme is deactivated by heating at 95° C. for five minutes. Then the oligonucleotides Ia and Ib are hybridized with one another by heating them in aqueous solution at 95° C. for 2 minutes and then slowly cooling to 5° C.

The oligonucleotides Ic and Id, and Ie and If, are phosphorylated and hybridized in pairs analogously.

For the gene fragment II, the oligonucleotides IIa and IIb, and IIf and IIg, are hybridized in pairs, and the remaining oligonucleotides IIc, IId and IIe are hybridized together.

Ligation of the three paired oligonucleotides for gene fragment I and of the two paired oligonucleotides and the treble oligonucleotide for gene fragment II is carried out as follows:

The double-stranded oligonucleotides are combined and ligation is carried out in 40 µl each of 50 mM tris. HCl buffer, 20 mM magnesium chloride and 10 mM DTT using 100 units of T4-DNA ligase at 15° C. over the course of 16 hours.

Gene fragments I and II are purified by gel electrophoresis on a 15% strength polyacrylamide gel (without addition of urea, 20×40 cm, 1 mm thick), the marker substance used being X 174 DNA (supplied by BRL), cut with Hinf I.

3. Preparation of hybrid plasmids which contain the gene fragments I and II a) Incorporation of gene fragment I in pBR 322

The commercial plasmid pBR 322 is opened in a known manner using the restriction endonucleases EcoRI and PstI in accordance with the manufacturer's information. The digestion mixture is separated by electrophoresis on a 5% strength polyacrylamide gel in a known manner, and the fragments are visualized by staining with ethidium bromide or by radioactive labeling ("Nick translation" method of Maniatis, loc. cit.). The plasmid band is then cut out of the acrylamide gel and separated from the polyacrylamide by electrophoresis.

Ligation of 1 µg of plasmid with 10 ng of gene fragment I is then carried out at 16° C. overnight. The hybrid plasmid according to FIG. 1 is obtained.

b) Incorporation of gene fragment II in pUC 8

Figure 2:
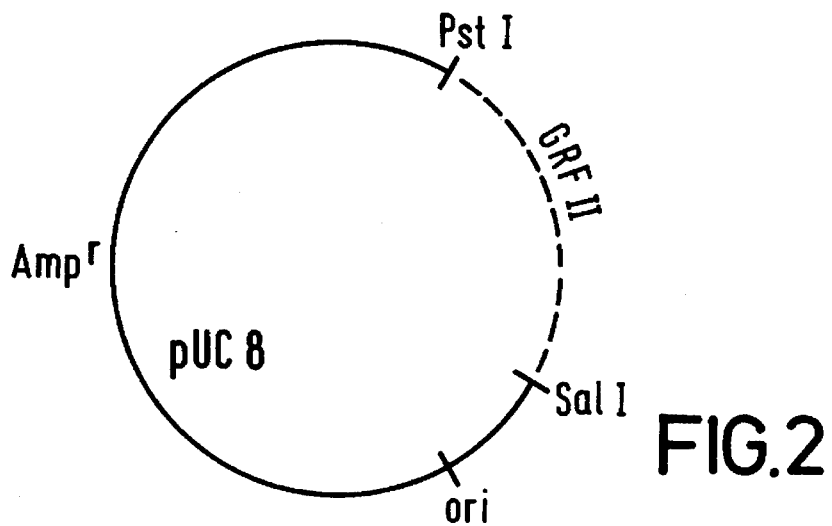
FIG. 2 shows the incorporation of gene fragment II of the GRF gene into plasmid pUC 8.

The commercial plasmid pUC 8 is cut open with PstI and SalI and ligation with gene fragment II is carried out in analogy to a). The hybrid plasmid according to FIG. 2 is obtained.

c) Incorporation of a modified gene fragment

It is also possible, in a manner corresponding to b), to incorporate a modified gene fragment II in which, in accordance with DNA sequence II, the codon for leucine is inserted in nucleotide triplet No. 27. This modified gene fragment II is obtained by an appropriately modified synthesis of structural units IIa and IIb of the gene, the sequence ATG in structural unit IIa being replaced by CTG and, correspondingly, the sequence TAC in structural unit IIb of the gene being replaced by GAC.

4. Synthesis of the complete gene a) Transformation and amplification

The hybrid plasmids thus obtained are transferred into *E. coli*. For this purpose, the strain *E. coli* K 12 is made competent by treatment with a 70 mM calcium chloride solution, and the suspension of the hybrid plasmid in 10 mM tris.HCl buffer (pH 7.5) or 70 mM calcium chloride solution is added. The transformed strains are selected by using the resistance or sensitivity to antibiotics conferred by the plasmid, and the hybrid vectors are amplified, in a customary manner. After killing the cells, the hybrid plasmids are isolated, cut open using the restriction enzymes originally employed, and the gene fragments I and II are isolated by gel electrophoresis.

b) Linkage of the gene fragments

The gene fragments Ia and Ib obtained by amplification are linked enzymatically as described in Example 2, and the synthetic gene having DNA sequence I thus obtained is introduced into cloning vectors.

5. Synthesis of hybrid plasmids which contain the complete gene a) Incorporation in pKK 177.3

The expression plasmid pKK 177.3 (plasmid ptac 11, Amman et al., Gene 1983, 167–178, in which a sequence containing a SalI cutting site has been incorporated synthetically into the EcoRI recognition site) is opened using the restriction enzymes EcoRI and SalI, and ligation with the synthetic gene corresponding to DNA sequence I is carried out. This entails the introduced gene being placed behind the regulation region of plasmid pKK 177.3. After addition of a suitable inducer, such as isopropyl-β-thiogalactopyranoside (IPTG), a mRNA which leads to expression of the polypeptide Met-GRF-Gly is formed.

b) Incorporation in pWH1

Figure 3:
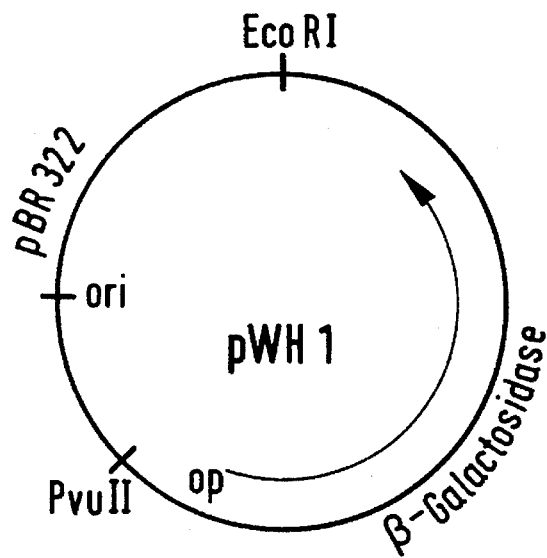
FIG. 3 shows plasmid pWH 1 which contains the beta-galactosidase gene and a portion of plasmid pBR 322.

The expression plasmid pWH 1 comprises a pBR 322 portion and the gene for β-galactosidase, with its regulation region (FIG. 3). To prepare it, 10 µg of pBR 322 are cut using the restriction endonucleases EcoRI and PvuII, and separation is carried out by electrophoresis in 5% strength polyacrylamide gel. After visualization of the DNA bands using ethidium bromide (or by radioactive labeling), the larger band (2292 base-pairs) is cut out of the gel, and polyacrylamide is removed by electroelution. The gene for β-galactosidase is split out of a Lac-transduced phage, such as λ or φ 80 dlac, by digestion with EcoRI and partial digestion with PvuII. A fragment of approximately 3185 nucleotide pairs is isolated in analogy to the work-up described above. This fragment bears the intact regulation region of the Lac operon and the genetic information for β-galactosidase with aminoacids 1 to 1005. Ligation of this Lac-DNA fragment into the DNA fragment from plasmid pBR 322 results in the plasmid pWH 1 having the regulation region of the Lac operon, the coding sequence for β-galactosidase (aminoacids 1 to 1005), the ampicillin-resistance gene of pBR 322, and the replication region of pBR 322. The natural regulation region of the Lac operon can be replaced by any desired synthetic regulation regions, such as, for example, tac. This plasmid contains a unique EcoRI cutting site at aminoacid 1005 of β-galactosidase, and this can be used as a cloning site for eukaryotic genes.

Ligation of a chemically synthesized linker which contains the recognition sequences for the restriction enzymes SalI and EcoRI:

```
5'-TCGACGCCCG
   GCGGGCTTAA - 5'
``` onto DNA sequence I is carried out. After digestion with the restriction enzyme EcoRI, a DNA fragment flanked by EcoRI recognition sequences is obtained. A fragment of this type can then be integrated into the plasmid pWH1 which has been opened with EcoRI.

For this purpose, pWH1 is opened with EcoRI and dephosphorylated at the 5' ends of the EcoRI cutting site using bacterial alkaline phosphatase. By this means, ligation of the plasmid with itself is prevented, and there is a considerable reduction in the "background" of transformed bacterial cultures containing non-recombinant plasmid. The only plasmids which can be closed to form a circle are those which have integrated a gene fragment with flanking EcoRI recognition sequences.

6. Transformation of the hybrid plasmids

Competent *E. coli* cells are transformed with 0.1–1 μg of plasmid pWH1 which has undergone ligation with 10 μg of GRF gene, and are plated out on ampicillin-agar plates. The integration of the GRF gene and its direction of integration in the plasmid can then be determined by DNA rapid work-up (Maniatis, loc.cit.).

7. Expression

After transfer of these hybrid plasmids into *E. coli*, a fused protein which bears the 1005 aminoacids of β-galactosidase on the amino end of the Met-GRF sequence is expressed. A GRF-Gly derivative is obtained after cleavage with cyanogen bromide.

Modified GRF proteins are obtained in analogy to this, for example the product in which leucine replaces methionine as aminoacid No. 27.

8. Working up and purification

The bacterial strains which have been cultured to the desired optical density are induced using a suitable inducer, for example IPTG, for an adequate time, for example 2 hours. Then the cells are killed using 0.1% cresol and 0.1 mM phenylmethylsulfonyl fluoride (benzylsulfonyl fluoride). After centrifugation or filtration, the mass of cells is digested in acidic aqueous solution at pH 3.0 in a suitable apparatus (French press or Dyno® mill), whereupon the insoluble constituents are removed by centrifugation. The proteins are isolated from the supernatant using the method of Guillemin (loc.cit). The enrichment and the purity of the products are checked by HPLC analysis.

The methionine (together with the portion of the bacterial protein, such as β-galactosidase, which is bonded to the methionine in fused proteins) is removed by cleavage with cyanogen bromide, and the GRF derivative is extracted under acid conditions and is purified (Guillemin, loc.cit.).

Fused proteins containing β-galactosidase can be detected by gel electrophoresis even on the crude extract from the lysed bacteria by means of the difference in their migration behavior from that of authentic β-galactosidase. After cleavage with cyanogen bromide, the purity and enrichment of the GRF derivative and its variants are determined by HPLC as mentioned above.

The GRF activity in the products can be characterized by immunological and biological methods, as follows:

In a radioimmunoassay, the bacteriologically prepared GRF and its variants react with an antibody against synthetic GRF having the aminoacid sequence 1–44. The radioimmunoassay is advantageously designed as an indirect immunoprecipitation assay with anti-GRF antibodies and anti-IgG-anti-GRF antibodies. The sensitivity of the RIA is 10 ng of GRF.

In the biological assay, the bacteriologically prepared product and its variants are tested for release of growth hormone in rats. For this purpose, the product or its variants are administered intravenously to anesthetized rats, and the release of the growth hormone in the blood of the rat is determined radioimmunologically.

DNA I17 D

|    |    |    |    |    |    | 0 Met | 1 Tyr 10 | 2 Ala | 3 Asp 15 |
|----|----|----|----|----|----|-------|----------|-------|----------|
|    |    |    |    | 5' | AA | ATG   | TAC      | GCT   | GAC      |
|    |    |    |    | 3' | G  | TAC   | ATG      | CGA   | CTG      |

| 4 Ala 20 | 5 Ile | 6 Phe 25 | 7 Thr | 8 Asn 30 | 9 Ser 35 | 10 Tyr | 11 Arg 40 | 12 Lys | 13 Val 45 |
|----------|-------|----------|-------|----------|----------|--------|-----------|--------|-----------|
| GCT      | ATC   | TTC      | ACT   | AAC      | TCT      | TAC    | CGT       | AAA    | GTT       |
| CGA      | TAG   | AAG      | TGA   | TTG      | AGA      | ATG    | GCA       | TTT    | CAA       |

| 14 Leu 50 | 15 Gly | 16 Gln 55 | 17 Leu | 18 Ser 60 | 19 Ala 65 | 20 Arg | 21 Lys 70 | 22 Leu | 23 Leu 75 |
|-----------|--------|-----------|--------|-----------|-----------|--------|-----------|--------|-----------|
| CTG       | CGT    | CAG       | CTG    | TCT       | GCT       | CGT    | AAA       | CTG    | CTG       |
| GAC       | CCA    | GTC       | GAC    | AGA       | CGA       | GCA    | TTT       | GAC    | GAC       |

| 24 Gln 80 | 25 Asp | 26 Ile 85 | 27 Met | 28 Ser 90 | 29 Arg 95 | 30 Gln | 31 Gln 100 | 32 Gly | 33 Glu 105 |
|-----------|--------|-----------|--------|-----------|-----------|--------|------------|--------|------------|
| CAG       | GAC    | ATC       | ATG    | TCT       | AGA       | CAG    | CAG        | GGT    | GAA        |
| GTC       | CTG    | TAG       | TAC    | AGA       | TCT       | GTC    | GTC        | CCA    | CTT        |

| 34 Ser 110 | 35 Asn | 36 Gln 115 | 37 Glu | 38 Arg 120 | 39 Gly 125 | 40 Ala | 41 Arg 130 | 42 Ala | 43 Arg 135 |
|------------|--------|------------|--------|------------|------------|--------|------------|--------|------------|
| TCT        | AAC    | CAG        | GAA    | CGT        | GGT        | GCT    | CGA        | GCT    | CGT        |
| AGA        | TTG    | GTC        | CTT    | GCA        | CCA        | CGA    | GCT        | CGA    | GCA        |

| 44 Leu 140 | 45 Gly | 46 Stp 145 | 47 Stp 149 |     |     |
|------------|--------|------------|------------|-----|-----|
| CTG        | GGT    | TAA        | TAG        |     | 3'  |
| GAC        | CCA    | ATT        | ATC        | AGC T | 5' |

DNA II17 E

| 0 | 1 | 2 | 3 | 4 | 5 | 6 | 7 | 8 | 9 | 10 | 11 | 12 | 13 |
|---|---|---|---|---|---|---|---|---|---|---|---|---|---|
| ATG | 1A1 | GCT | GAC | GCT | ATC | TTC | ACT | A2C | TCT | TAC | CGT | A2A | 2TT |
| Met | Tyr | Ala | Asp | Ala | Ile | Phe | The | Asn | Ser | Tyr | Arg | Lys | Val |
|  | His |  |  |  |  |  |  | Ser |  |  |  | Arg | Ile |

| 14 | 15 | 16 | 17 | 18 | 19 | 20 | 21 | 22 | 23 | 24 | 25 | 26 | 27 |
|---|---|---|---|---|---|---|---|---|---|---|---|---|---|
| CTG | GGT | CAG | CTG | T31 | GCT | CGT | AAA | CTG | CTG | CA4 | GA3 | ATC | 3TG |
| Leu | Gly | Gln | Leu | Ser | Ala | Arg | Lys | Leu | Leu | Gln | Asp | Ile | Met |
|  |  |  |  | Tyr |  |  |  |  |  | His | Glu |  | Leu |

| 28 | 29 | 30 | 31 | 32 | 33 | 34 | 35 | 36 | 37 | 38 | 39 | 40 | 41 |
|---|---|---|---|---|---|---|---|---|---|---|---|---|---|
| abc | AGA | CAG | CAG | CGT | GAA | deT | AAC | CAG | GAA | Clm | 5GT | GCT | CGA |
| Ser | Arg | Gln | Gln | Arg | Glu | Ser | Asn | Gln | Gly | Arg | GLy | Ala | Arg |
| Asn |  |  |  |  |  | Arg |  |  |  | Gln | Arg |  |  |

| 42 | 43 | 44 | 45 | 46 | 47 |
|---|---|---|---|---|---|
| fg1 | hi1 | CTG | CGT | TAA | TAG |
| Ala | Arg | Leu | Gly | Stp | Stp |
| Phe | Asn |  |  |  |  |

```
1 = T    C        abc = TCT              AAC
2 = A    G        de = TC                CG
3 = C    A        fg = GC                TT
4 = G    T        hi = AA                CG
5 = G    C        lm = AA, AG, GA, GG    GT
```

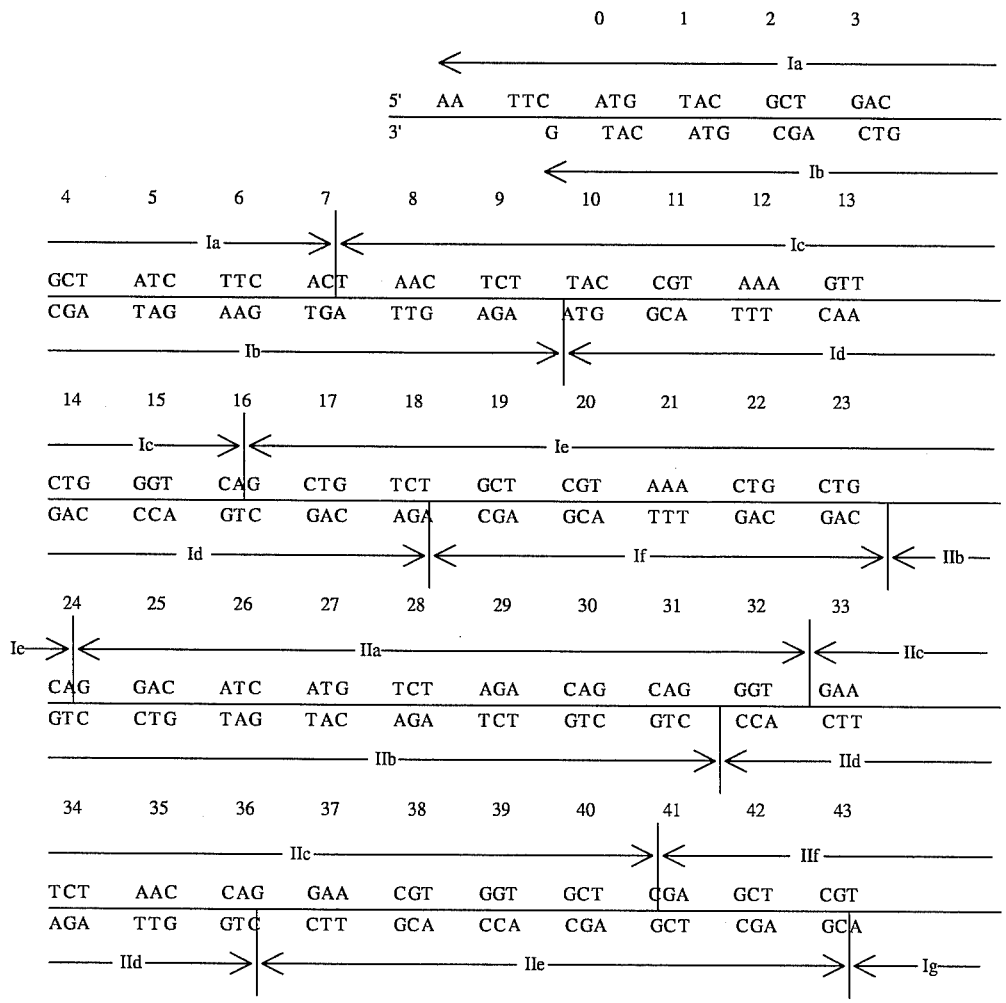

DNA III17 F

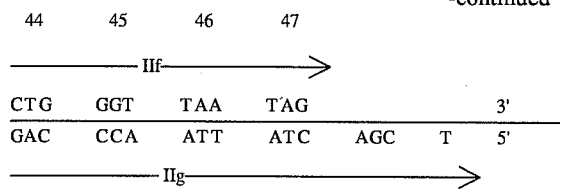

We claim:

1. A process for the preparation of a polypeptide carboxamide of the formula I $$H-Y-R-NH_2 \qquad (I)$$

in which R is a peptide sequence of genetically codable amino acids having a carboxyl-terminal Leu, Y is methionine or a bacterial protein sequence coupled via methionine to the amino end of said peptide sequence R, which comprises producing a polypeptide of the formula II $$H-Y-R-NH-CH_2-COOH \qquad (II)$$

by recombinant DNA methods and converting the polypeptide of formula II by enzymatic cleavage into the polypeptide carboxamide of formula I.

2. The process as claimed in claim 1, wherein a polypeptide of formula II, in which R does not contain methionine, is produced by recombinant DNA methods and then the said Y is removed by cleavage with cyanogen bromide.

3. The process as claimed in claim 1, wherein R is the amino acid sequence of growth hormone releasing factor (GRF).

4. The process as claimed in claim 2, wherein R is a modified GRF sequence in which the methionine at amino acid number 27 ($Met^{27}$) is replaced by leucine.

5. The process as claimed in claim 3, wherein R is the amino acid sequence of a modified GRF, the modification consisting of replacing one or more of the following naturally occuring amino acids:

$Tyr^1$ by His, $Asn^8$ by Ser, $Lys^{12}$ by Arg, $Val^{13}$ by Ile,
$Ser^{18}$ by Tyr, $Gln^{24}$ by His, $Asp^{25}$ by Glu, $Met^{27}$ by Leu,
$Ser^{28}$ by Asn, $Ser^{34}$ by Arg, $Arg^{38}$ by Gln, $Gly^{39}$ by Arg,
$Ala^{42}$ by Phe or $Art^{43}$ by Asn.

6. The process as claimed in claim 4, wherein R is the amino acid sequence of a modified GRF, the modification consisting of replacing one or more of the following naturally occuring amino acids:

$Tyr^1$ by His, $Asn^8$ by Ser, $Lys^{12}$ by Arg, $Val^{13}$ by Ile,
$Ser^{18}$ by Tyr, $Gln^{24}$ by His, $Asp^{25}$ by Glu, $Ser^{28}$ by Asn,
$Ser^{34}$ by Arg, $Arg^{38}$ by Gln, $Gly^{39}$ by Arg, $Ala^{42}$ by Phe,
or $Arg^{43}$ by Asn.

7. A DNA part sequence of the formula V

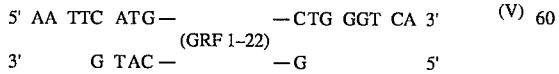

in which (GRF 1–22) stands for the codons for amino acid numbers 1 to 22 of GRF.

8. A DNA part sequence as claimed in claim 7, wherein the codons for the amino acid sequence are modified, the modification consisting of replacing one or more of the following naturally occuring amino acids:

$Tyr^1$ by His, $Asn^8$ by Ser, $Lys^{12}$ by Arg, $Val^{13}$ by Ile,
or $Ser^{18}$ by Tyr.

9. A DNA part sequence in the formula VI

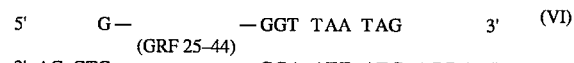

in which (GRF 25–44) stands for the codons for amino acid numbers 25 to 44 of GRF.

10. A DNA part sequence as claimed in claim 9, wherein the codons for the amino acid sequence are modified, the modification consisting of replacing one or more of the following naturally occuring amino acids:

$Asp^{25}$ by Glu, $Met^{27}$ by Leu, $Ser^{28}$ by Asn, $Ser^{34}$ by Arg,
$Arg^{38}$ by Gln, $Gly^{39}$ by Arg, $Ala^{42}$ by Phe or $Arg^{43}$ by Asn.

11. A DNA sequence of the formula VII

in which (GRF 1–n) stands for the codons for amino acid numbers 1 to n of GRF, n being 16 to 44.

12. A DNA sequence as claimed in claim 11, wherein (GRF 1–n) stands for the codons for amino acid numbers 1 to n of a modified GRF, n being 16 to 44 and the modification consisting of replacing one or more of the following naturally occuring amino acids:

$Tyr^1$ by His, $Asn^8$ by Ser, $Lys^{12}$ by Arg, $Val^{13}$ by Ile,
$Ser^{18}$ by Tyr, $Gln^{24}$ by His, $Asp^{25}$ by Glu, $Met^{27}$ by Leu,
$Ser^{28}$ by Asn, $Ser^{34}$ by Arg, $Arg^{38}$ by Gln, $Gly^{39}$ by Arg,
$Ala^{42}$ by Phe or $Art^{43}$ by Asn.

13. A hybrid plasmid containing a DNA sequence as defined in claim 7.

14. A hybrid plasmid containing a DNA sequence as defined in claim 8.

15. A hybrid plasmid containing a DNA sequence as defined in claim 9.

16. A hybrid plasmid containing a DNA sequence as defined in claim 10.

17. A hybrid plasmid containing a DNA sequence as defined in claim 11.

18. A hybrid plasmid containing a DNA sequence as defined in claim 12.

19. A transformed bacterial cell which contains a hybrid plasmid as claimed in claim 13.

20. A transformed bacterial cell which contains a hybrid plasmid as claimed in claim 14.

21. A transformed bacterial cell which contains a hybrid plasmid as claimed in claim 15.

22. A transformed bacterial cell which contains a hybrid plasmid as claimed in claim 16.

23. A transformed bacterial cell which contains a hybrid plasmid as claimed in claim 17.

24. A transformed bacterial cell which contains a hybrid plasmid as claimed in claim 18.

25. A transformed *E. coli* cell which contains a hybrid plasmid as claimed in claim 13.

26. A transformed *E. coli* cell which contains a hybrid plasmid as claimed in claim 14.

27. A transformed *E. coli* cell which contains a hybrid plasmid as claimed in claim 15.

28. A transformed *E. coli* cell which contains a hybrid plasmid as claimed in claim 16.

29. A transformed *E. coli* cell which contains a hybrid plasmid as claimed in claim 17.

30. A transformed *E. coli* cell which contains a hybrid plasmid as claimed in claim 18.

* * * * *